US00PP34438P2

(12) United States Plant Patent
Sills et al.

(10) Patent No.: US PP34,438 P2
(45) Date of Patent: Jul. 26, 2022

(54) BLACKBERRY PLANT NAMED 'DRISBLACKTWENTYNINE'

(50) Latin Name: ***Rubus* L. subgenus *Rubus***
Varietal Denomination: 'DrisBlackTwentyNine'

(71) Applicant: Driscoll's, Inc., Watsonville, CA (US)

(72) Inventors: Gavin R. Sills, Watsonville, CA (US); Yunwen Wang, Watsonville, CA (US); Mark F. Crusha, Watsonville, CA (US); John Fangary, Watsonville, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 17/570,234

(22) Filed: Jan. 6, 2022

(51) Int. Cl.
*A01H 6/74* (2018.01)
*A01H 5/08* (2018.01)

(52) U.S. Cl.
USPC ..... Plt./203

(58) Field of Classification Search
USPC ..... Plt./203
See application file for complete search history.

(56) References Cited

U.S. PATENT DOCUMENTS

| | | | |
|---|---|---|---|
| PP6,679 | P | 3/1989 | Moore |
| PP6,782 | P | 5/1989 | Jennings |
| PP13,525 | P3 | 1/2003 | Fear et al. |
| PP13,758 | P3 | 5/2003 | Fear et al. |
| PP13,759 | P3 | 5/2003 | Fear et al. |
| PP14,682 | P3 | 4/2004 | Fear et al. |
| PP14,765 | P2 | 5/2004 | Cook et al. |
| PP14,780 | P2 | 5/2004 | Cook et al. |
| PP15,058 | P2 | 8/2004 | Cook et al. |
| PP17,162 | P3 | 10/2006 | Moore et al. |
| PP17,983 | P2 | 9/2007 | Cabrera |
| PP22,002 | P2 | 7/2011 | Pabon et al. |
| PP22,449 | P3 | 1/2012 | Clark |
| PP23,497 | P3 | 3/2013 | Clark et al. |
| PP23,725 | P3 | 7/2013 | Sills et al. |
| PP24,249 | P3 | 2/2014 | Clark |
| PP24,609 | P3 | 7/2014 | Rodriguez et al. |
| PP24,701 | P3 | 7/2014 | Rodriguez et al. |
| PP24,878 | P2 | 9/2014 | Alcazar et al. |
| PP25,502 | P3 | 5/2015 | Pabon et al. |
| PP26,501 | P3 | 3/2016 | Pabon et al. |
| PP26,611 | P3 | 4/2016 | Pabon et al. |
| PP26,774 | P3 | 5/2016 | Pabon et al. |
| PP27,129 | P2 | 9/2016 | Sills et al. |
| PP27,130 | P2 | 9/2016 | Sills et al. |
| PP27,146 | P2 | 9/2016 | Sills et al. |
| PP27,681 | P3 | 2/2017 | Sills et al. |
| PP27,746 | P3 | 3/2017 | Sills et al. |
| PP28,548 | P2 | 10/2017 | Sills et al. |
| PP31,110 | P2 | 11/2019 | Sills et al. |
| PP31,291 | P2 | 12/2019 | Sills et al. |
| PP31,825 | P2 | 6/2020 | Sills et al. |
| PP31,826 | P2 | 6/2020 | Sills et al. |
| PP32,268 | P2 | 10/2020 | Sills et al. |
| PP33,067 | P2 | 5/2021 | Sills et al. |
| PP33,068 | P2 | 5/2021 | Sills et al. |
| PP33,088 | P2 | 5/2021 | Sills et al. |

OTHER PUBLICATIONS

Voss, Donald H. The Royal Horticultural Society Colour Chart 2001 Journal American Rhododendron Society, vol. 56, No. 1 2002 3 pages.

Williams, et al. DNA polymorphisms amplified by arbitrary primers are useful as genetic markers Nucleic Acids Research, vol. 18, No. 22 1990 pp. 6531-6535.

*Primary Examiner* — Annette H Para
(74) *Attorney, Agent, or Firm* — Morrison & Foerster LLP

(57) ABSTRACT

A new and distinct variety of blackberry plant named 'DrisBlackTwentyNine', particularly selected for its plant health, fruit size, firmness, and flavor, as well as yield, is disclosed.

4 Drawing Sheets

LATIN NAME:

Botanical classification: *Rubus* L. subgenus *Rubus*.

Varietal denomination: The varietal denomination of the claimed variety of blackberry plant is 'DrisBlackTwenty-Nine'.

BACKGROUND OF THE INVENTION

Blackberry is the common name for a multitude of plant species bearing dark purple to black aggregate fruit in the genus *Rubus* of the family Rosaceae. Most blackberries are within the subgenus *Rubus*.

Native chiefly to the northern temperate regions, blackberries are now being cultivated as a valuable fruit crop in many areas of the world, particularly in Europe, North America and Central America. Recognized for their high contents of antioxidants, dietary fiber, vitamin C, and vitamin K. Blackberry fruit are typically consumed as fresh fruit, individually quick frozen fruit, or in prepared foods, such as purées, juices, jellies, jams, grocery items, baked goods, and snack foods.

Globally, Mexico is the leading producer of blackberries, with nearly the entire crop being produced for export into the off-season fresh markets in North America and Europe. The Mexican market is almost entirely from the cultivar 'Tupi' (also spelled as 'Tupy'). In the United States, Oregon is the leading commercial blackberry producer, followed by the state of California.

Blackberries are perennial plants that typically bear biennial stems (known as "canes") from a perennial root system. The two cane types are primocanes, or first-year canes, which are usually vegetative, and floricanes, which are the same canes and produce fruit in the next growing season. In its first year, a new cane, the primocane, grows vigorously to its full length of three to six meters in a growth habit of erecting, arching, or trailing along the ground and bearing large compound leaves with 3, 5, or 7 leaflets; it does not produce any flowers. In its second year, the cane becomes a floricane and stops elongating, but the lateral buds break to produce flowering laterals that bear fruit.

Recently, primocane-fruiting blackberry varieties have been developed that are capable of flowering and fruiting on first-year canes. Primocane-fruiting blackberry varieties have several advantages, including potential of two crops on the same plant in the same year, reduction in pruning costs by mowing of canes, avoidance of winter injury, and production of fruit in an extended geographic area. However, primocane-fruiting blackberry varieties are also subject to a number of challenges, such as poor heat tolerance, lesser fruit quality, and low yield.

Blackberry is an important and valuable commercial fruit crop. Accordingly, there is a need for new varieties of blackberry plant. In particular, there is a need for improved varieties of blackberry plant that are stable, high yielding, and agronomically sound.

SUMMARY OF THE INVENTION

In order to meet these needs, the present invention is directed to an improved variety of blackberry plant. In particular, the invention relates to a new and distinct variety of blackberry plant (*Rubus* L. subgenus *Rubus*), which has been denominated as 'DrisBlackTwentyNine'.

Blackberry plant variety 'DrisBlackTwentyNine' was selected in Santa Cruz, Calif. in June of 2013 and originated from a controlled cross between the proprietary female parent blackberry plant 'BN972.1' (unpatented) and the male parent blackberry plant 'DrisBlackEighteen' (U.S. Plant Pat. No. 31,110). The original seedling of the new variety was first asexually propagated via root cuttings in Santa Cruz, Calif. in October of 2013.

'DrisBlackTwentyNine' was subsequently asexually propagated via root cuttings, and underwent testing in Santa Cruz, Calif. from 2015 to 2021 (six years). The present variety has been found to be stable and reproduce true to type through successive asexual propagations via root cuttings and tissue culture.

'DrisBlackTwentyNine' was selected for its plant health, fruit size, firmness, and flavor, as well as yield.

BRIEF DESCRIPTION OF THE DRAWINGS

This new blackberry plant is illustrated by the accompanying photographs. The colors shown are as true as can be reasonably obtained by conventional photographic procedures. The photographs are of plants that are two to five years old.

DETAILED BOTANIC AL DESCRIPTION

Figure 1:
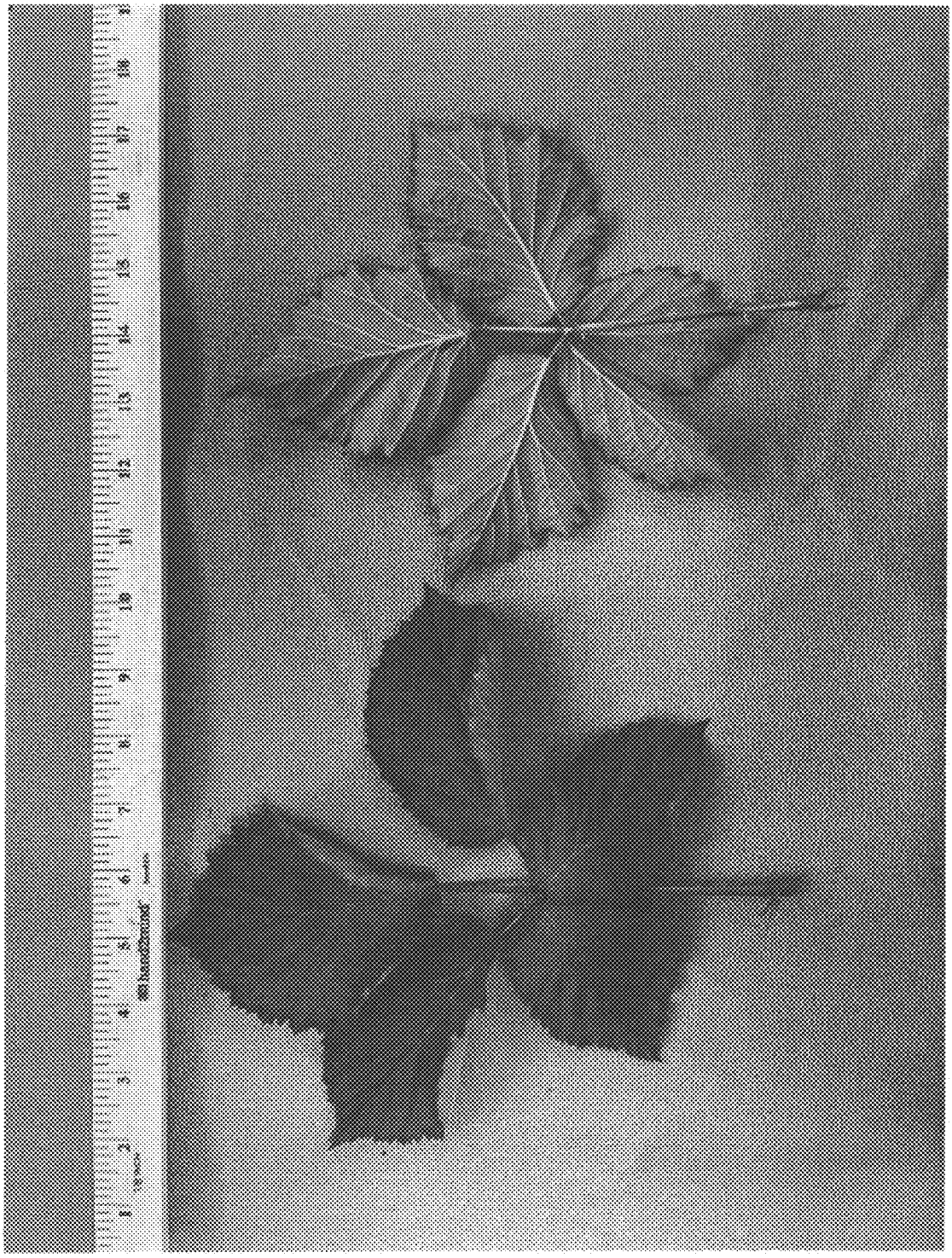
FIG. 1 illustrates leaves of variety 'DrisBlackTwentyNine'.
Figure 2:
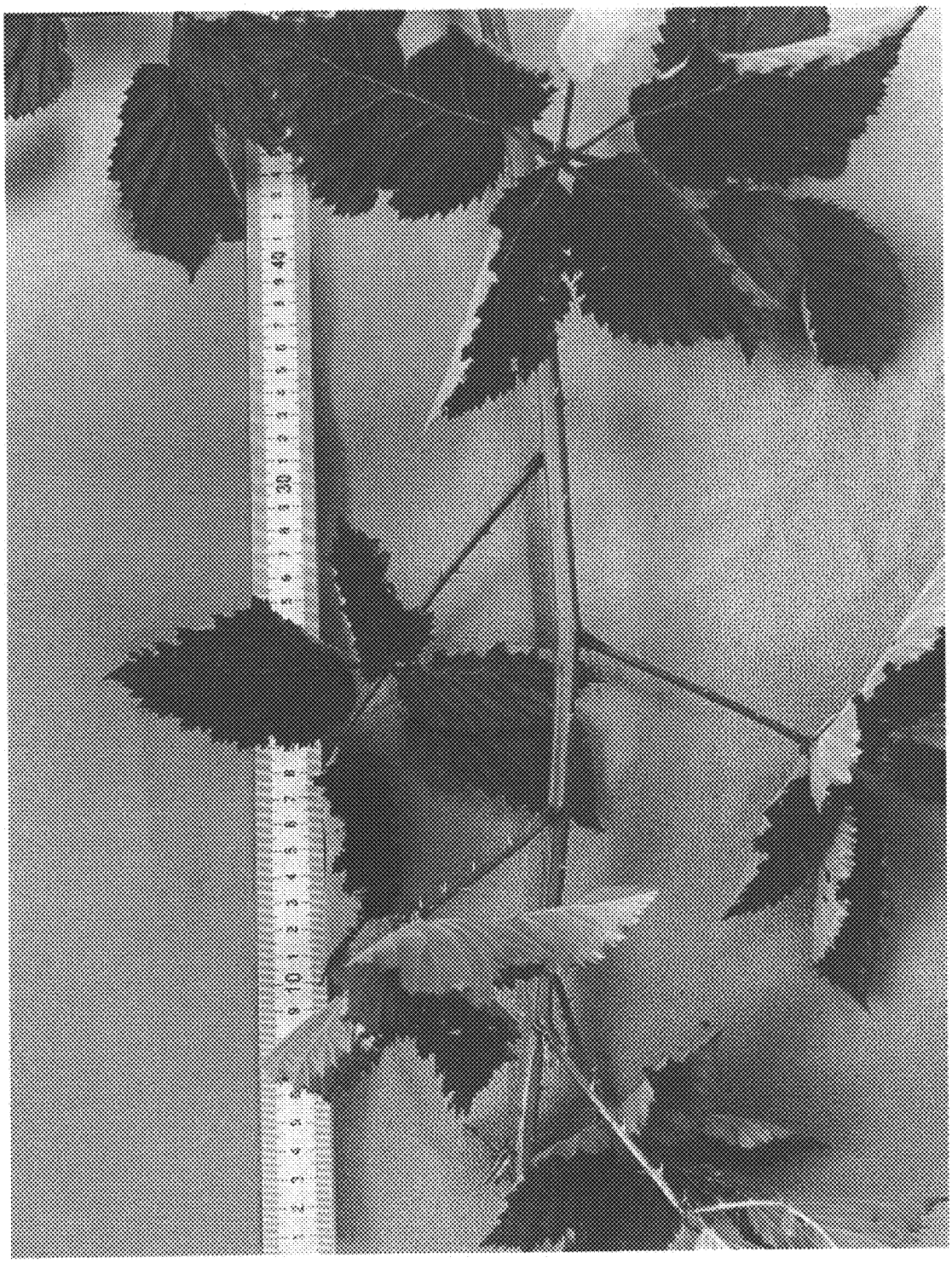
FIG. 2 illustrates a section of a cane of variety 'DrisBlackTwentyNine'.
Figure 3:
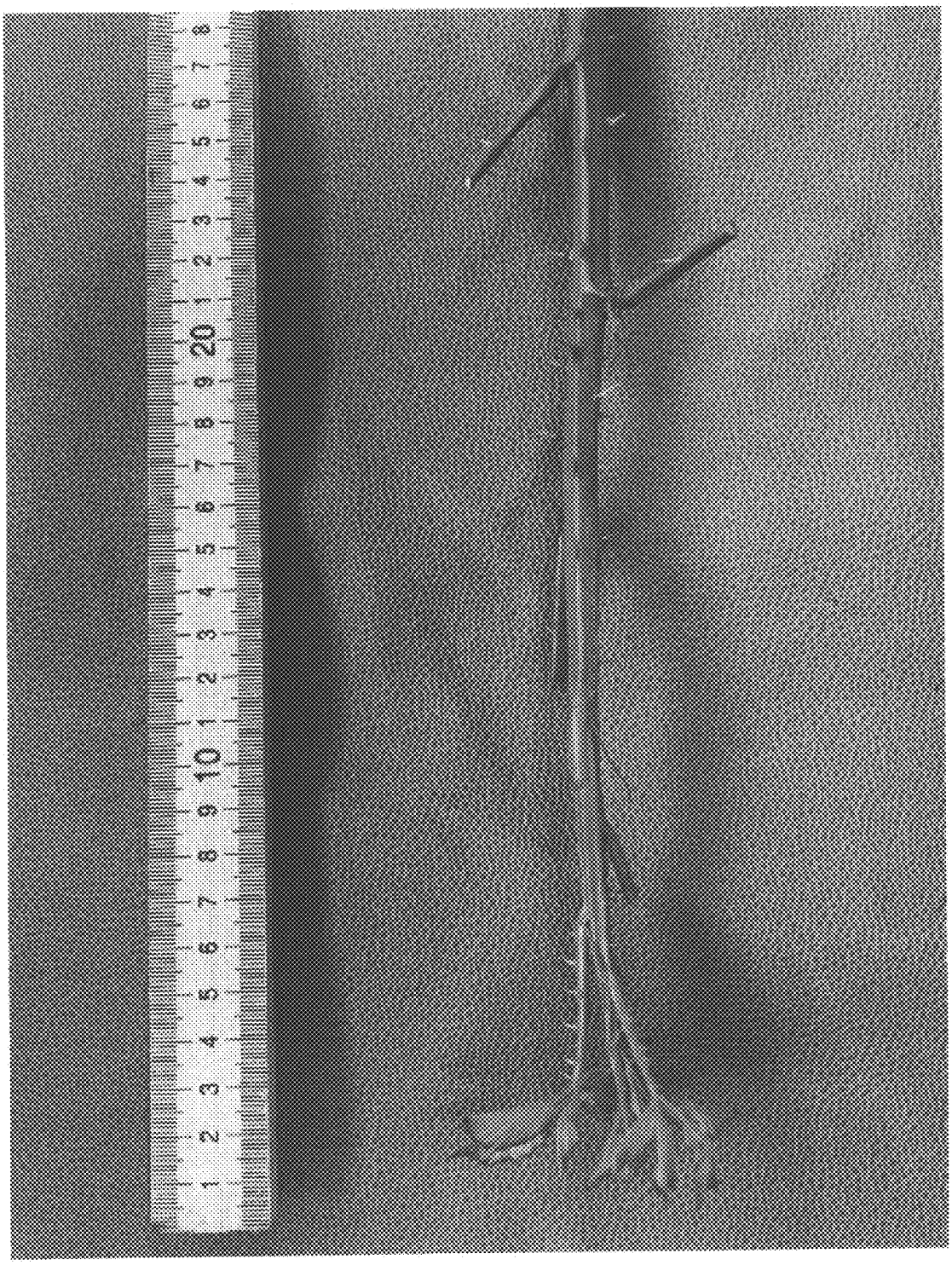
FIG. 3 illustrates a young shoot of variety 'DrisBlackTwentyNine'.
Figure 4:
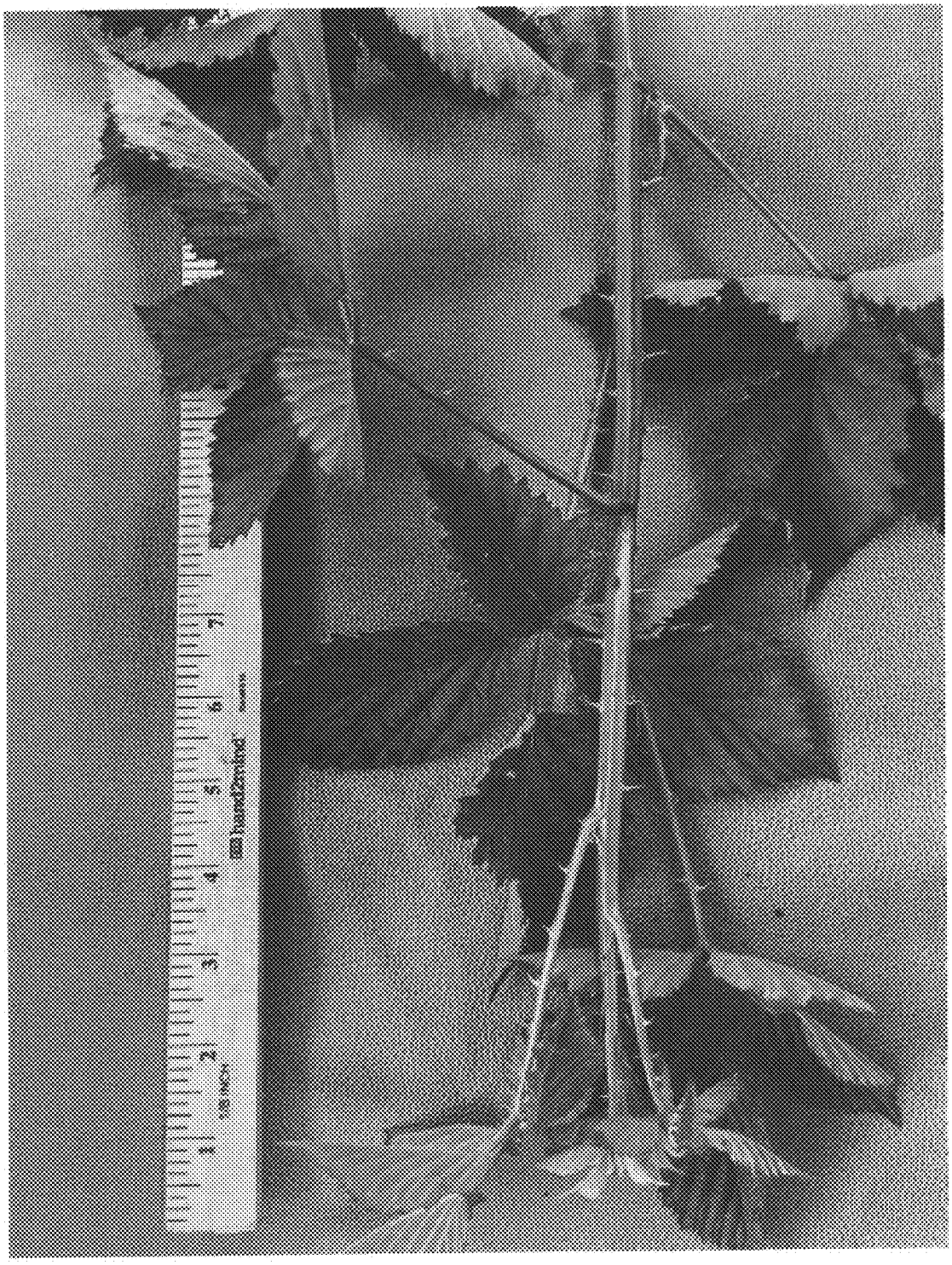
FIG. 4 illustrates a young shoot of variety 'DrisBlackTwentyNine'.

The following descriptions set forth the distinctive characteristics of 'DrisBlackTwentyNine'. The data that define these characteristics are based on observations taken in Santa Cruz, Calif. from 2015 to 2021. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwentyNine' has not been observed under all possible environmental conditions. The botanical description of 'DrisBlackTwentyNine' was taken from plants that were two to five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* $2^{nd}$ edition by James G. Harris and Melinda Woolf Harris, unless where otherwise defined.

Classification:

*Family*.—Rosaceae.

*Botanical*.—*Rubus* L. subgenus *Rubus*.

*Common name*.—Blackberry.

*Variety name*.—'DrisBlackTwentyNine'.

Parentage:

*Female parent*.—'BN972.1' (unpatented).

*Male parent*.—'DrisBlackEighteen' (U.S. Plant Pat. No. 31,110).

Plant:

*Propagation*.—Root cuttings and tissue culture.

*Growth habit*.—Upright.

*Height*.—212.3 cm.

*Width*.—32.6 cm.

*Height/width ratio*.—6.51.

*Vigor*.—Medium.

*Self-fruitfulness*.—Self-fruitful.

Canes:

*Internodal distance*.—7.2 cm.

*New cane*.—Number of new canes: Medium. Strength: Strong. Glaucosity (waxy bloom): Strong.

*Dormant cane*.—Length: Medium. Diameter (in central third): Medium. Anthocyanin coloration: Medium. Number of branches: Medium. Predominant distribution of branches: Over whole length. Cross-section: Angular. Spines: Present. Number of spines: Medium. Length: 8.7 mm. Width (at base): 1 mm. Density of spines (on central third of cane): Medium. Texture: Medium hardness. Attitude of apex (in relation to cane): Outwards.

*Fruiting lateral*.—Fruiting lateral length ($4^{th}$ lateral from tip): 64.6 cm.

*Young shoots*.—Length: 92.5 cm. Diameter: 1 cm. Number of young shoots: Medium. Anthocyanin coloration (during rapid growth): Medium. Intensity of green color: Medium. Number of glandular hairs: Absent or few.

Leaves:

*Time of leaf bud burst*.—Medium.

*Leaf*.—Predominant number of leaflets: 5. Type: Palmate. Relative position of lateral leaflets: Free. Venation: Cross-venulate. Intensity of green color of upper side: Medium. Intensity of green color of lower side: Medium. Profile in cross-section: Concave (margins rolled inwards). Glossiness of upper side: Medium.

*Leaflet*.—Type of incision of margin: Bi-serrate. Depth of margin incisions: Medium.

*Terminal leaflet*.—Length: 10.09 cm. Width: 7.1 cm. Length/width ratio: 1.42. Shape: Ovate. Base: Obtuse. Margin: Doubly serrate. Lobing: Absent. Shape in cross-section: U-shaped. Blistering between veins: Medium.

*Lateral leaflet* (*single leaflet in basal pair*).—Length: 9 cm. Width: 6 cm. Length/width ratio: 1.5. Shape: Ovate. Base: Obtuse. Margin: Doubly serrate.

*Rachis* (*length between terminal leaflet and adjacent lateral leaflets*).—4.5 cm.

*Petiole*.—Length: 9.9 cm. Diameter: 2.5 mm. Pigmentation of upper surface: Medium. Pigmentation of lower surface: Medium. Size of stipules: Medium.

*Stipule*.—Length: 1 cm. Width: 1 mm. Orientation: Erect.

Inflorescence:

*Flower*.—Fragrance: Very faint or absent.

*Petal*.—Color: White. Shape: Oval. Apex: Emarginate. Base: Attenuate. Margin: Erose.

Fruit:

*Yield*.—14,000 pounds (lbs) to 31,600 pounds (lbs) of fruit per acre per season from 24-36 month-old plants when grown in Watsonville, Calif.

Resistance to pests and diseases:

*Redberry mite* (*acalitus essigi*).—Moderately susceptible.

*Fusarium wilt* (*fusarium oxysporum*).—Moderately resistant.

COMPARISON TO PARENTAL AND REFERENCE BLACKBERRY VARIETIES

'DrisBlackTwentyNine' differs from the proprietary female parent 'BN972.1' in that 'DrisBlackTwentyNine' has a higher yield potential compared to 'BN972.1'.

'DrisBlackTwentyNine' differs from the male parent 'DrisBlackEighteen' (U.S. Plant Pat. No. 31,110) in that 'DrisBlackTwentyNine' has spines present on dormant cane, medium anthocyanin coloration on young shoots during rapid growth, U-shaped cross section of the terminal leaflet, and the number of glandular hairs on the young shoot is absent or few, whereas 'DrisBlackEighteen' has spines absent on dormant cane, weak anthocyanin coloration on young shoots during rapid growth, V-shaped cross section of the terminal leaflet, and the number of glandular hairs on the young shoot is medium. 'DrisBlackTwentyNine' also has higher vigor compared to 'DrisBlackEighteen'.

'DrisBlackTwentyNine' differs from the reference variety 'DrisBlackSix' (U.S. Plant Pat. No. 25,502) in that 'DrisBlackTwentyNine' has an upright growth habit, medium anthocyanin coloration on dormant cane, medium anthocyanin coloration on young shoots (during rapid growth), and the dormant cane length is medium, whereas 'DrisBlackSix' has a semi-upright growth habit, strong anthocyanin coloration on dormant cane, strong anthocyanin coloration on young shoots (during rapid growth), and the dormant cane length is long.

'DrisBlackTwentyNine' differs from the reference variety 'DrisBlackSeventeen' (U.S. Plant Pat. No. 31,291) in that 'DrisBlackTwentyNine' has an upright growth habit, medium anthocyanin coloration on dormant cane, medium anthocyanin coloration on young shoots (during rapid growth), and the attitude of spine apex in relation to cane is outwards, whereas 'DrisBlackSeventeen' has a semi-upright growth habit, weak anthocyanin coloration on dormant cane, absent or very weak anthocyanin coloration on young shoots (during rapid growth), and the attitude of spine apex in relation to cane is upwards.

What is claimed is:

1. A new and distinct variety of blackberry plant designated 'DrisBlackTwentyNine' as shown and described herein.

* * * * *